US011071505B2

(12) United States Patent
Schaefer et al.

(10) Patent No.: US 11,071,505 B2
(45) Date of Patent: Jul. 27, 2021

(54) ANATOMY ADAPTED ACQUISITION WITH FIXED MULTI-SOURCE X-RAY SYSTEM

(71) Applicant: KONINKLIJKE PHILIPS N.V., Eindhoven (NL)

(72) Inventors: Dirk Schaefer, Hamburg (DE); Michael Grass, Buchholz in der Nordheide (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 260 days.

(21) Appl. No.: 16/099,217

(22) PCT Filed: May 8, 2017

(86) PCT No.: PCT/EP2017/060857
§ 371 (c)(1),
(2) Date: Nov. 6, 2018

(87) PCT Pub. No.: WO2017/194434
PCT Pub. Date: Nov. 16, 2017

(65) Prior Publication Data
US 2020/0315556 A1    Oct. 8, 2020

(30) Foreign Application Priority Data
May 11, 2016   (EP) .................................. 16169084

(51) Int. Cl.
*A61B 6/00*    (2006.01)
*A61B 6/12*    (2006.01)
(52) U.S. Cl.
CPC .............. *A61B 6/4014* (2013.01); *A61B 6/12* (2013.01); *A61B 6/4028* (2013.01);
(Continued)

(58) Field of Classification Search
None
See application file for complete search history.

(56) References Cited

U.S. PATENT DOCUMENTS

2005/0008210 A1    1/2005   Evron
2006/0008047 A1*   1/2006   Zhou ..................... A61B 6/032
                                                        378/10
(Continued)

FOREIGN PATENT DOCUMENTS

DE    102010040308 A1   3/2012
WO    2003077763 A2     9/2003
WO    2015063191 A1     5/2015

OTHER PUBLICATIONS

Movassaghi, B. et al, "A Quantitative Analysis of 3-D Coronary Modeling from two or more Projection Images" IEEE Transaction on Medical Imaging, vol. 23, No. 12, pp. 1517-1531, Dec. 2004.
(Continued)

*Primary Examiner* — Edwin C Gunberg

(57) ABSTRACT

A system (SC) for controlling operation of a multi-focal-spot X-ray imager (IA). The system comprises a projection direction determiner (PDD) configured to determine a projection direction for an object (OB) to be imaged, based on a geometric structure of a model m(OB) for the object (OB). A selector (SX) of the system is configured to select, from the imager (IA)'s plurality of focal-spot-detector pairs (IPj) with different optical axes (OXj), at least one target pair whose optical axis corresponds to the determined projection direction.

17 Claims, 3 Drawing Sheets

(52) U.S. Cl.
CPC .......... *A61B 6/4266* (2013.01); *A61B 6/4464* (2013.01); *A61B 6/487* (2013.01); *A61B 6/545* (2013.01)

(56) References Cited

U.S. PATENT DOCUMENTS

| | | |
|---|---|---|
| 2008/0171936 A1 | 7/2008 | Homan |
| 2009/0257559 A1 | 10/2009 | Urushiya |
| 2010/0315487 A1 | 12/2010 | Grassin |
| 2013/0064343 A1 | 3/2013 | Verstraelen |
| 2015/0036799 A1 | 2/2015 | Zhang |
| 2016/0106382 A1 | 4/2016 | Lu |
| 2016/0106387 A1 | 4/2016 | Kahn |
| 2017/0322484 A1* | 11/2017 | Erhard ................. G03B 42/026 |

OTHER PUBLICATIONS

Chen, S.J. et al "3-D Reconstruction of Coronary Arterial Tree to Optimize Angiographic Visualization", IEEE Transaction on Medical Imaging, vol. 19, No. 4, Apr. 2000.

* cited by examiner

ANATOMY ADAPTED ACQUISITION WITH FIXED MULTI-SOURCE X-RAY SYSTEM

CROSS-REFERENCE TO PRIOR APPLICATIONS

This application is the U.S. National Phase application under 35 U.S.C. § 371 of International Application No. PCT/EP2017/060857, filed on May 8, 2017, which claims the benefit of European Patent Application No. 16169084.7, filed on May 11, 2016. These applications are hereby incorporated by reference herein.

FIELD OF THE INVENTION

The invention relates to a system for controlling operation of a multi-focal-spot X-ray imager, to a method of controlling operation of a multi-focal-spot X-ray imager, to an imaging arrangement, to a computer program element and to a computer readable medium.

BACKGROUND OF THE INVENTION

Multi-source x-ray imaging with a single embodiment detectors have been considered for interventional use. One such multi-source imaging system is disclosed in WO 2015/063191. Several issues have however been reported with these types of multi-source x-ray imagers. Some limitations arise due to limited detector frame speed in the case where a single detector is used for instance. Other issues include x-ray dose or cross scatter when using such multi-source x-ray imagers.

SUMMARY OF THE INVENTION

There may therefore be a need to address some or all of the shortcomings described above.

The object of the present invention is solved by the subject matter of the independent claims where further embodiments are incorporated in the dependent claims. It should be noted that the following described aspect of the invention equally applies to the method of controlling operation of a multi-focal-spot X-ray imager, to the imaging arrangement, to the computer program element and to the computer readable medium.

According to a first aspect of the invention there is provided an imaging arrangement comprising a multi-focal spot X-ray imager of the non-rotational type, having a detector and an X-ray source unit defining a plurality of focal spots, the source unit being configured so that the focal spots define, with the detector, imaging pairs having different optical axes.

The arrangement further comprises a projection direction determiner configured to determine a projection direction for an object to be imaged based on a geometric structure of a model for the object and a selector configured to select, from the plurality of imaging pairs, at least one target pair whose optical axis is within an angular margin $\Delta\alpha$ of the determined projection direction.

Thus, there exists a "correspondence" between the optical axis of the selected imaging pair and the determined, optimal, projection direction such that the optical axis deviates least, or in any case by less than a given margin, from at least one of the projection directions or from an (possibly weighted) average of all determined projection directions (in case the projection direction determiner returns more than one projection direction).

According to one embodiment, the system comprises an instruction module configured to instruct the imager to acquire an image of the object along the optical axis of the target pair. The proposed system is particularly beneficial where a sequence of frames is to be acquired at different instants such as during a fluoroscopic or angiographic intervention or other. In particular, a frame for a given imaging instant is only acquired along optical axis or axes of the selected target imaging pair(s). The selection may be dynamically adapted during acquisition of the sequence. Only a true subset of all available imaging pairs is selected at any given imaging instant. This allows reducing the number of projections as only a (true) sub-set of imaging pair is selected from all possible imaging pairs. In on embodiment, as an extreme case, only a single imaging pair is selected at some or all imaging instants. Image quality and relevance is maintained however as the selection is based on the geometric structure of the object of interest. Frame rate can be increased in particular in imagers where a single detector is used In particular the frame rate for the currently selected viewing direction can be increased because interleaved acquisitions along (other) imaging directions are avoided. Cross-scatter can also be increased as fewer X-ray beams are crossing each other at any given imaging instant.

According to one embodiment, the selection is dynamically adapted by use of a model a model updater configured to update the model. The projection direction determiner then (possibly) determines a new projection direction and/or the selector then selects a new target pair based on the newly determined projection direction. The model is updated in particular when shape changes or re-orientations of the object are detected.

According to one embodiment, the determining of the projection direction by the projection direction determiner is based on any one or a combination of the following selection criteria: i) an amount of perspective foreshortening of the model or a part thereof in projection view, ii) an amount of perspective overlap of features of the model in projection view, or iii) a deviation from a normal vector of a plane defined by a geometric configuration of the model.

According to one embodiment, the X-ray source unit includes a plurality of different X-ray sources, together defining a system of fixed sources, each having a respective focal spot, situated at different positions in respect of the subject/objet or the examination region of the imager.

According to another embodiment, the X-ray source unit includes at least one X-ray source having a spatially variable focal-spot. In particular, the X-ray source may have a movable focal spot within a single vacuum tube, which is movable for example by deflecting an electron beam It is also possible to combine these embodiments, i.e. a plurality of movable focal spot X-ray sources may be used, which sources are in a predefined, fixed arrangement with one another.

The imager is of the non-rotational type, that is the detector and/or the X-ray source unit (but preferably both) is/are mounted in a fixed spatial configuration/arrangement. In particular neither the X-ray source nor the detector moves during the imaging. This allows cost conscious construction as expensive mechanical equipment (motors, actuators, etc.) can be left out. In particular, the mutual spatial relationship between the X-ray source unit and the detector is held fixed by one or more suitable mounting structure(s), frame(s), brackets, etc.

According to another aspect, there is provided a method of controlling operation of an X-ray imaging apparatus operable in a plurality of imaging pairs (IP) defined by a plurality of X-ray focal spots and a detector (D), the imaging pairs having different optical axes, the method comprising the steps of:

for an object to be imaged, determining a projection direction based on a geometric structure of a model for the object; and selecting, from the plurality of imaging pairs, a target pair whose optical axis is within an angular margin $\Delta\alpha$ of the determined projection direction.

According to one embodiment, the method further comprises:

acquiring an image of the object along the optical axis of the selected focal-spot-detector pair. Specifically, the image at a given image instant is acquired only along the optical axis of the target pair or pairs.

According to one embodiment, the method further comprises:

updating the model and determining a new projection direction and/or selecting a new target pair.

According to one embodiment, the determining of the projection direction is based on any one or a combination of the following selection criteria: i) an amount of perspective foreshortening of the model or a part thereof in projection view, ii) an amount of perspective overlap of features of the model in projection view, or iii) a deviation from a normal vector of a plane defined by a geometric configuration of the model.

According to another aspect, there is provided a computer program element, which, when being executed by a processing unit, is adapted to perform the steps of a method as per any one of the above mentioned embodiments.

According to another aspect, there is provided a computer readable medium having stored thereon the program element.

Definitions

"Object model" as used herein is preferably a 3D representation (a mesh model or a line model or any other suitable representation) for a tool (guidewire, artificial heart valve or other) or contrast agent or any other foreign object that resides in a subject during imaging. In addition or instead the model may be 3D representation of an internal anatomic feature of the subject. In particular, the model may be configured as a combo or super-model that represents features of both, the tool or foreign object in addition with some anatomic features in the surroundings of the object.

The term "imaging pair" or "focal-spot-detector pair" relates to a specific detector and focal spot combination usable for imaging along a specific optical axis. Two focal-spot-detector-pairs differ in the focal spot, and optionally also in the detector (if the imager has more than one detector). Specifically, an imager with a single detector and n (n≥2) focal spots will give rise to n different focal-spot pairs.

BRIEF DESCRIPTION OF THE DRAWINGS

Exemplary embodiments of the invention will now be described with reference to the following drawings wherein.

DETAILED DESCRIPTION OF EMBODIMENTS

Figure 1:
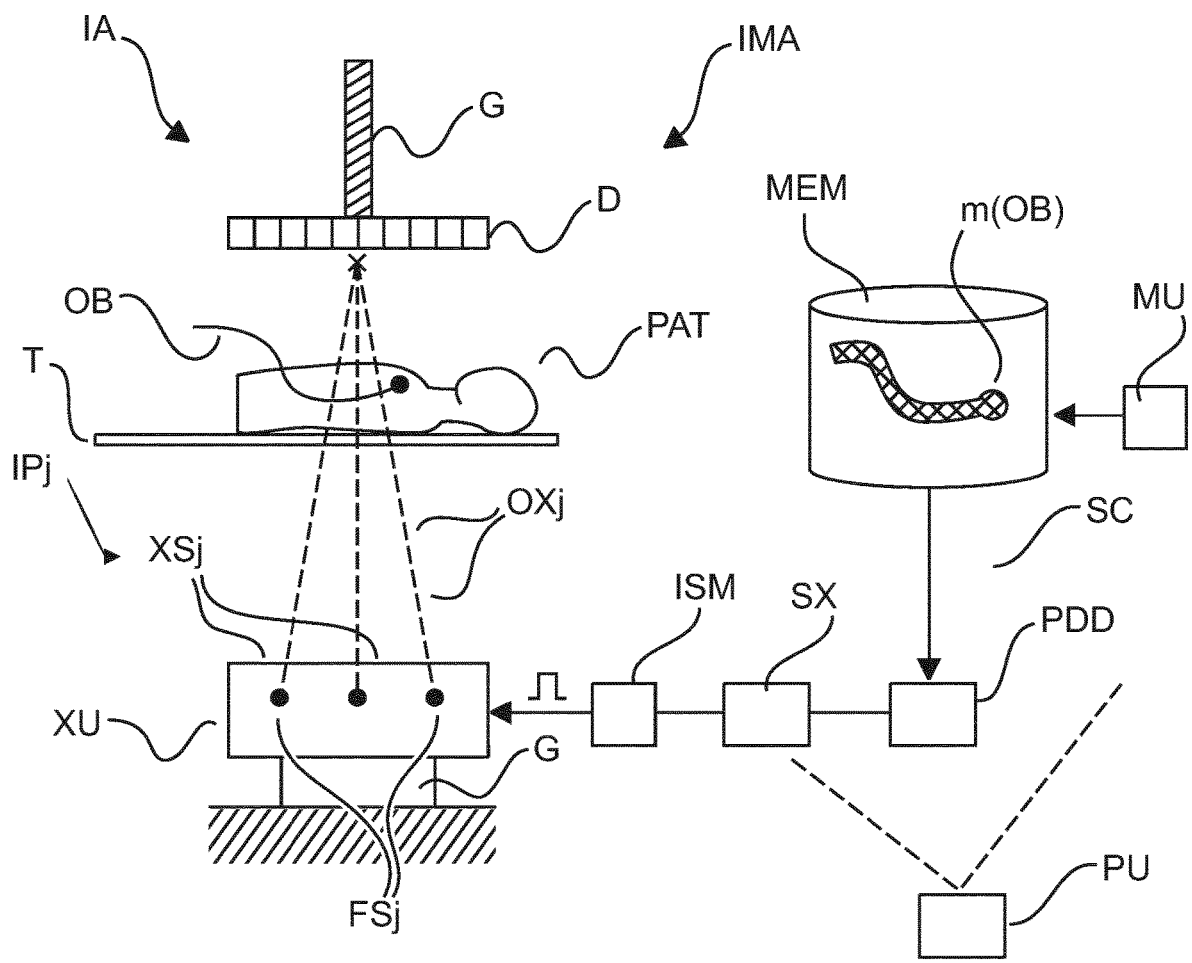
FIG. 1 shows an imaging arrangement.

With reference to FIG. 1, there is shown a schematic block diagram of an imaging arrangement IMA comprising an X-ray imaging apparatus IA and a system SC for controlling operation of the imaging apparatus IA (referred to herein as the "imager").

Applications of the imaging arrangement IMA envisaged herein include medical interventions where one or more objects OB such as a medical tool (catheters, guide wires, etc.) is/are introduced into a subject PAT, such as a human or animal patient.

The imager IA allows acquiring images of the inside of the patient PAT to verify position or orientation, etc., of the introduced object OB. For example's sake, the object may be a guide wire for use in cardiac intervention. The guide wire OB is introduced into the patient at a suitable entry point and is then forwarded to a target site such as valve of the heart. The guide wire is flexible and its flexure in particular the bending of its tip portion can be controlled from the outside by the interventional surgeon (user) via a mechanism to perform various tasks. Examples for this include TAVI (Trans-catheter Aortic Heart Valve) procedures such as deploying an artificial heart valve where an ailing heart valve is being replaced by an artificial valve which is delivered as a "collapsed package" which expands once deployed at the correct site. Other examples are repair procedures such as mitral valve repair to mitigate regurgitation. In some instances of mitral valve repair, a catheter delivered clip is applied to pinch (and permanently hold together) valve leaflets of the mitral valve. Stent placement procedures are also envisaged. In any of these procedures, a guide wire is used.

In any of these or similar procedures, navigational precision and spatial awareness is called for, and the imager IA facilitates this by acquiring a still image or preferably a series of images (frames) to so provide in real time image supported guidance for the user to verify position against the surrounding anatomy of the tool OB.

Although in the following main reference will be made for the tool being a guide wire OB, this does not exclude other objects and indeed applications of the proposed imaging arrangement in other fields of medicine or in fact in non-medical fields such as exploration of inaccessible cavities, non-destructive material testing or baggage screening at airports, etc. are also envisaged herein in alternative embodiments.

Turning now in more detail to the imager IA, this includes an x-ray source unit XU and a detector D capable of detecting X-ray radiation emittable by the X-ray source unit XU during imaging. The imager may include a single detector D (as shown in FIG. 1) or a plurality of detectors.

The x-ray unit XU and the detector are arranged opposite to each other and spaced apart from each other to form an examination region in which there is situated an examination support T such as a table.

On the table and hence in the examination region, subject PAT is situated during the imaging and in particular during the intervention whilst the guide wire OB resides in subject PAT.

During imaging, the x-ray unit is energized to produce x-ray radiation that propagates from the x-ray unit XU through the patient PAT and then impinges on the detector D. The detector unit D is preferably of the flat panel type. Direct or indirect conversion technologies are envisaged herein in different embodiments. In either embodiment, the detector includes a plurality of radiation sensitive pixel elements which together form a radiation sensitive surface. The impinging X-ray radiation is converted into electrical signals by these pixel elements. The electrical signals are processed by a suitable analogue-to-digital conversion circuitry to produce one or a series (a "stream") of images ("frames"). The images are made up from pixel values (that is, numbers) obtained from the A/D conversion and these are arranged in respective 2D arrays for each image.

Depending on the exact imaging modality used, the pixel values represent a quantity of interest. For instance, in projective radiography mainly envisaged herein, the pixel values represent the amount of attenuation experienced by the X-ray radiation in its passage through the patient. In one embodiment as mainly envisaged herein, image contrast represents attenuation by absorption but other contrasts across the pixel values are also envisaged where the pixel values encode other quantities such as phase contrast, attenuation by scatter (e.g. in dark-field imaging), etc. For the latter, the imager may include suitable interferometric equipment (e.g., gratings) and suitably configured signal processing backend to extract the desired information. The frames so produced are then passed onto a visualizer which effects rendering a graphics display of these images on a display device such as a monitor (not shown). The images also encode information of the tool OB residing in the subject during the imaging. It is ensured that the material of the object has sufficient radio-opacity to ensure an appreciable projective footprint in the imagery. Additional materials may be introduced in the subject to elicit contrast, such as liquid contrast agent as is done in angiography and envisaged herein in some embodiments. Specifically, a defined quantity ("bolus") of this liquid is injected prior to imaging into the patient PAT and this confers contrast to blood vessels (such as the coronaries in cardiac imaging) in the images as it propagates through the patient's blood vessels. This is because blood vessels in particular would otherwise fail to produce sufficient contrast, at least in absorptive radiography.

Although still imagery is not excluded herein, preferably a stream of frames at a suitable frame rate fps (frames per sec). Suitable frames rates are about 10-30, in particular 15, (or even in the 100's, such as 200), but these numbers are not limiting, The frames are rendered for display in sequence on the display device MT to generate a moving picture which allows the user to verify in real-time the position of the guide wire OB. However, that is not to say that the proposed imaging arrangement is restricted to real-time live imagery as the images which are produced may be stored for later review in a memory (such as a database in a hospital information system (HIS) or a in picture archive system PACS) or the images may be otherwise processed (filtered, shared, transmitted, etc.).

The imager IA is of the non-rotational type. In other words, the x-ray imager IA may include a fixed mounting structure G. In the fixed mounting structure G envisaged herein, there is no motion of the imager's X-ray source unit and/or of the detector D during imaging when the imager operates to acquire the stream of images. By way of the (one or more) mounting structure G, the X-ray unit XU and/or the detector D is floor or ceiling mounted or may be mounted on a stand, etc. The detector module D and/or the X-ray unit XU are mounted relative to each other at a distance to define the examination region. In particular in the embodiment shown in FIG. 1, the detector D is ceiling mounted or stand mounted above the examination region, in particular above patient support T, whilst the X-ray unit is mounted on the same or a separate mounting structure under the patient support T. Alternatively, it is the X-ray source unit XU that is mounted above table T and the detector unit D is mounted under the table T.

Turning now in more detail to the X-ray unit XU of the imager IA, this is envisaged herein to be configured to provide multi-focal-spot imaging capability. This can be achieved in one embodiment by the x-ray unit XU including a plurality of different, discretely spaced x-ray sources each having their own vacuum tube. The individual x-ray sources are preferably housed in a single housing although this may not be necessarily so in all embodiments. That is, in some alternative embodiments, one or more (or in fact all) of the x-ray sources $XS_j$ have their own respective housing.

In an alternative embodiment, the multi-focal spot imaging is achieved by using a single x-ray source with spatially variable focal-spot. This can be achieved for instance by re-orienting the tube's anode disc relative to the tube's cathode to assume different positions within the vacuum tube to so define different focal spots because an electron beam emitted by the cathode will impact on the anode at different positions. Preferably however, electron optical arrangements are used to switchably deflect the tube's electron beam to that the electron beam from the cathode impacts on the anode at different positions, thus defining the different focal spots. "Hybrid" solutions are also envisaged herein, where one or more of the x-ray sources have a fixed focal-spot while one or more others have spatially variable focal spots. In yet other embodiments, a single (or two or more) X-ray tube is used that has more than one focal spots in the same vacuum tube and these focal spots are fixed. This can be achieved in one embodiment by having within the same vacuum tube more than two cathodes.

In sum, in any of the above mentioned embodiments, a system of two or more, discrete, spatially distributed focal spots $FS_j$ are defined, each situated (situatable) at different spatial positions relative to detector D. The one or more X-ray sources $XS_j$ are so configured that, when energized, a respective X-ray beam propagates from a respective focal spot FSj along different optical axis $OX_j$ toward the detector D, depending on the position of the respective focal-spot $FS_j$.

More particularly, the X-ray unit is preferably so configured that the various optical axes $OX_j$ are non-parallel to form a bundle of diverging axes $OX_j$. Said differently, the axes are relatively inclined to each other and so are the X-ray beams propagating along these axes $OX_j$. As shown in a schematic fashion in the left hand part of FIG. 1, each optical axis $OX_j$ (three are shown in dashed lines in FIG. 1) defines a respective, different, detector-focal-spot pair $IP_j$ (three are shown in FIG. 1). Preferably, the maximum achievable relative inclination between the optical axes $OX_j$ is between 30°-90° in caudo-cranial direction and LAO (left anterior oblique)-RAO (right anterior oblique) direction.

For brevity's sake, each detector-focal-spot pair $IP_j$ will also be referred to herein as an "imaging pair" $IP_j$. The relative, mutual inclinations of the optical axes $OX_j$ can be achieved for instance by mounting the different X-ray tubes XSj in mutual inclination to each other. Alternatively, and as described above, the electron optical arrangement or similar is used to deflect the electron beam accordingly and to so realize the different inclinations of the optical axes OXj for each imaging pair $IP_j$.

As shown in side elevation view in FIG. 1, a single detector unit D is used but other embodiments are also envisaged where there is plurality of separate detector units (either housed separately in different housings or housed in an integrated fashion in a single housing). In the later case, each imaging pair is then formed by a one of the detectors from the plurality of detectors and by one of the X-ray sources $XS_j$, or, more generally, by one of the different focal spot $FS_j$ positions.

The multi-focal-spot-imaging as envisaged herein allows acquiring different projection views of the object OB or region of interest (ROI) where the object is currently situated although the detector and/or the x-ray source(s) $XS_j$ of the unit XU is/are not moved relative to the object OB to be imaged. In other words, unlike rotational imaging systems such as CT or C-arm systems, multiple of projection views (each corresponding to the respective imaging pair $IP_j$) can be acquired although the x-ray source(s) and/or the detector (preferably both) reside throughout the imaging at respective, fixed, spatial positions. During operation of the multi-focal imager IA, that is, during acquisition of the stream of images at different acquisition instants t, different one(s) of the imaging pairs may be used.

Figure 2:
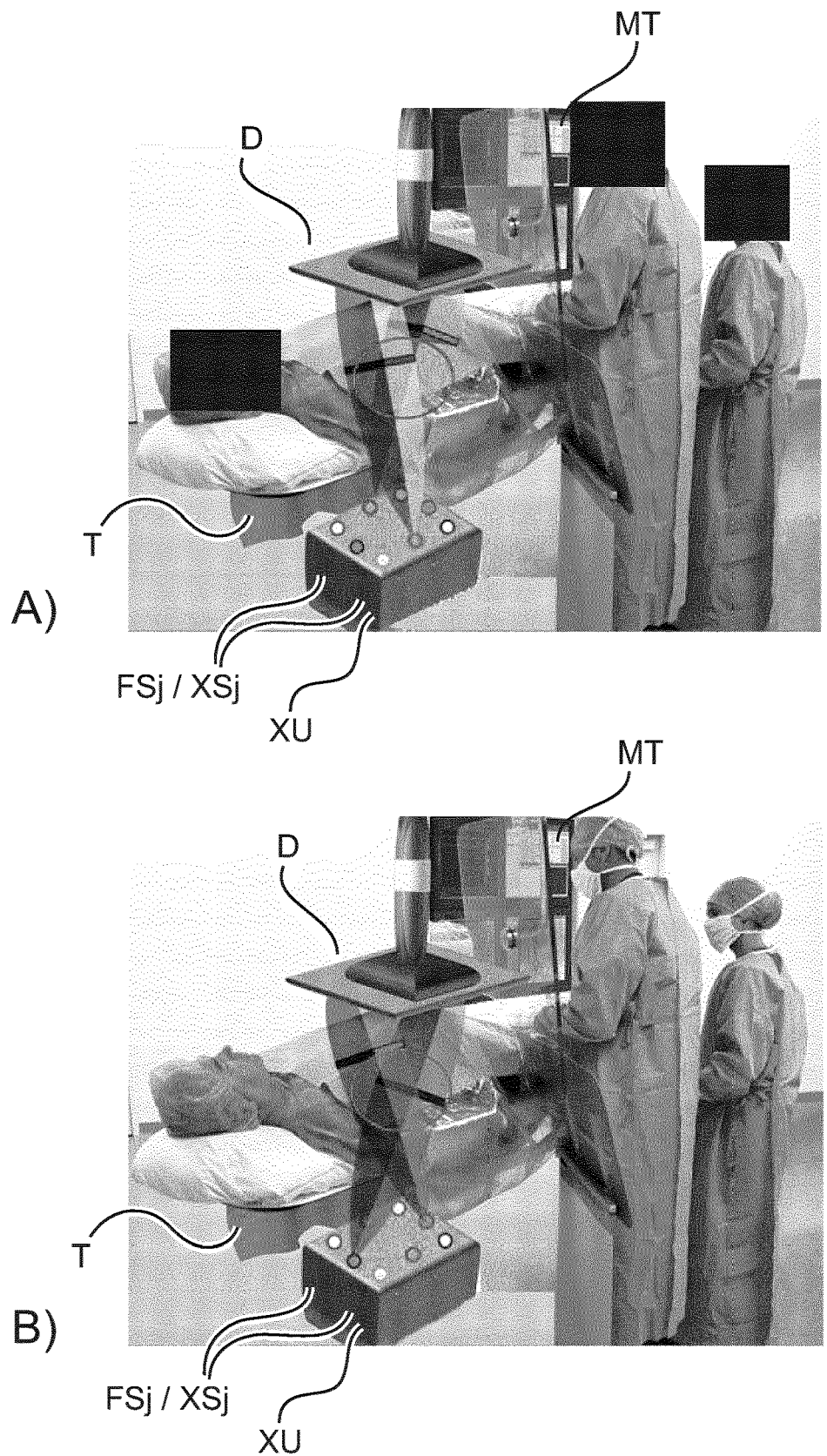
FIG. 2 shows different instances of image acquisition with a multi-focal X-ray imaging apparatus.

This is illustrated in the perspective view on the imager IA afforded by FIGS. 2A,B. In this, non-limiting, embodiment, the x-ray unit XU ("or multi-focal-x-ray block") includes eight different x-ray sources $XS_j$ indicated by different dots. At each imaging instant, a different pair of imaging pairs $IP_j$ (in this case, X-ray sources $XS_j$) is used. The sources are arranged in a rectangular (e.g., square) layout pattern, and at each imaging instant, imaging pairs IP are used whose X-ray sources are opposite each other in said pattern, e.g. are diagonally across or on opposing edges of the rectangular layout pattern. Alternatively, the sources may be arranged in other layout patterns, such a circular, elliptic, etc. In variation to the FIG. 2 embodiment, only a single imaging pair may be used at any imaging instant in some embodiments. This may be the case in particular when the single source with movable focal spot is used.

As further variant, to the imaging protocol in FIG. 2, at each instant, more than two of the imaging pairs $IP_j$ are used.

A combination of the above operation modes is also envisaged where at some instances a single imaging pair is used whereas in other instances two or more pairs are used for each imaging instant.

The black lines in FIG. 2 illustrate the respective beam diameters for each imaging pair. The respective circles in FIG. 2 indicate the area of where the X-ray beams cross each other when two imaging pairs are used at a time.

In one embodiment (but not necessarily in all embodiments), the imaging pairs $IP_j$ are arranged such that their respective, illuminatable volume intersect in 3D. This 3D intersection is called volume of interest (VOI). The imaged object is positioned in the VOI to ensure that it may be imaged from different perspectives with the selected imaging pair IP. In one embodiment, where a single detector is used, each imaging pair uses only a sub-region of the detector. That is, a specific sub-region of the detector may be associated with each focal spot, so that an imaging pair is defined between the focal spot and its associated sub-region. Thus, after a target pair has been selected, readout of the detector during subsequent imaging may be automatically limited to the respective sub-region, thus enabling a relatively high imaging frame rate.

A decision on which of the imaging pairs $IP_j$ is to be used for each imaging instant is taken by control system SC (shown to the right of FIG. 1) as proposed herein and to which now reference is made in more detail. Broadly, and as will be explained in more detail below, the control system SC allows selecting a (possibly different) sub-set of the imaging pairs to be used for any given imaging instant. The selection is based on a geometric structure of a model for the object OB. Yet more particularly, and in one embodiment, we propose to use a 3D representation of the object under consideration to select from the fixed projection directions the most appropriate projection direction. The proposed imaging arrangement allows in particular object adapted (e.g., anatomy adapted) image acquisition for fixed multi-focal spot (e.g., multi-source) X-ray imaging.

As previously mentioned above, the operation of the imaging control system SC is model based m(OB). The model m(OB) is a 3D representation of the object of interest such as a guide wire in a coronary vessel. The model can be generated in a preparatory phase in different ways all of which are envisaged herein.

A model for the object m(OB) may be generated by using a mesh generator as known from finite element analysis FEA and this is applied to model imagery of the object OB of interest to produce the mesh model m(OB). The model is envisaged as a 3D model. The mesh model may be surface model or a volume model. The model elements are for instance triangular elements or tetrahedral elements but the mesh elements may have any other geometrical shape. The model imagery from which the model m(OB) is taken may be obtained by a tri-angulation from at least two simultaneously acquired projections such as described by B. Movassaghi et al in "A quantitative analysis of 3-D coronary modeling from two or more projection images," IEEE Trans. Med. Im, vol. 23, no. 12, pp. 1517-1531 (2004). This can be done by using in FIG. 1 two of the imaging pairs IPj whose optical axes define a sufficiently wide angle (which can be less than 90°, e.g., 35°-90°, as described in Movassaghi et al). This imagery may be produced by the imager IA as used during in the intervention and this is indeed preferred. Alternatively, the model imagery may be produced by a different imaging modality such as from CT where the imagery is a registered pre-interventional volume data set. Once the model imagery is obtained, the relevant image portion may be shape-sensed by using model-based segmenter algorithms when the shape in 3D is known a priori such as is the case for the guidewire. The model may be stored in a memory MEM in a suitable data structure such as pointer structures, 3D-arrays or otherwise. Alternatively, the model m(OB) is not necessarily a mesh model. Specifically, a line model with known (or estimated) diameter can be used. Specifically, the line defines a geometrical centerline of the object, e.g. of the vessel branch or of the guidewire. A vessel model technique similar to section III, subsection B in Movassaghi may be used but applied not only to a vessel, but instead or in addition to the guidewire, catheter or other suitable, longitudinal tool with known, preferably uniform cross-section. However, other suitable model representations and related model generation techniques are also envisaged herein.

It will be understood, that the "object OB" of interest as used herein may not necessarily relate to the tool introduced, but may instead relate to the particular anatomy such as a cardiac vessel tree in angiographic imaging, the model thus being one of the respective anatomy. Combo or super-models are also envisaged that represent a tool in a particular anatomy or that represent the spatial relationship between two or more anatomic parts. In one particular embodiment, the model is that of a guide-wire in a coronary vessel.

What is seen here in one embodiment is to allow the orientation or shape of the model to change. This can be achieved by applying a mechanical simulation to the model of the guide wire for instance to model different shapes, for instance bending, flexing of the guidewire tip etc. In the same other use cases, other deformations such as expansion or compression may be modelled by the object model. For instance, in cardiac imaging, one may wish to have an object model for a TAVI valve. In particular the valve model may allow modeling deformations of the object to capture different states of compressions or expansions of the valve during deployment.

Now, given a current shape model m(OB) for a given imaging instant, operation of the control system SC will now be explained in more detail. As components, the system SC includes a projection direction determiner PDD, a selector module SX and an imaging instruction module ISM. The model is assumed to be registered to the imaging geometry of the particular imager IM, that is, coordinates/orientation of the X-ray unit, detector D and model are all aligned in a common coordinate system. Model registration can be achieved with existing registration tools. Based on the so registered given model for a particular shape of the model and for a giving imaging instant, the projection direction determiner PDD determines an optimal projection view on the model along an optimal projection direction. Optimality is measured against one or more optimality criteria which can be pre-programmed or user selected. The projection directions may be represented by suitable parameterization such as through one or more angular values measured relative to the common coordinate system. One or more optimal projection directions are then output projection determiner PDD for a given imaging instant.

The selector SX then selects one or more of the available imaging pairs $IP_j$ such that their respective optical axes $OX_j$ best match the determined projection directions. In particular, the (one or more) target pair $IP_j$ whose optical axis is within an (fixed or user defined) angular margin $\Delta\alpha$ of the determined, "ideal", projection direction is so selected. Only the single, angularly closest, projection direction is selected in one embodiment.

If the "pool" of optimal projection directions (as per the PDD projection direction determiner) comprises more than a single one, a respective target pair is selected as described, singly for each of the projection directions in the pool. Alternatively, the projection directions in the pool may be averaged into a single value and this "average direction" is then used to select the best matching pair IPj.

The instructor module ISM then interfaces with the imager IA to effect an image acquisition only along the selected ones of the imaging pairs for the given imaging instant. The instructor module instructs the imager AI to switch to the X-ray tube associated with the selected imaging pair or to operate the electron optical arrangement to deflect the electron beam to realize the selected imaging pair, etc.

Optionally, these computations may be re-run for the next imaging instant, once a shape change or motion of the object is detected. To this end, there is, optionally, a model adapter MU to adapt the model at different imaging instances to account for shape changes of the object OB or for reorientations of the object. The model of the object MOB is then adapted by the model updater MU. This can be done as mentioned above by running a mechanical simulation or by running an optimization procedure to fit the model to object's projection footprint as per the latest frame acquired or interpolated therefrom. For instance, in the guide wire embodiment, automatic tip tracking across the frames is used with repeated tri-angulation (as in the Movassaghi paper, referenced above or similar) to so achieve model adaptation.

Once the new model has been generated the projection determiner and the selector operate as previously described for the new model to produce, possibly (but not necessarily), a new selection of imaging pairs and for the subsequent imaging instant only these pair(s) IPj are/is then used.

In other words, as proposed herein, the selection of the imaging pairs is dynamically adapted to shape changes of the model by applying corresponding changes to the geometric structure of the object of interest and using the so adapted model in follow-up selections of the at least one imaging pair for imaging.

Different optimality criteria for the operation of the projection direction determiner PDD are envisaged herein. In one embodiment, one criteria is to find the direction where minimal foreshortening is experienced in the projection by the model m(OB) of object OB. Alternatively, all those directions are determined where the foreshortening falls below a suitably defined score value. For instance, the score may be determined by forming a ratio between a known length of the object (or of an estimate of the 3D length obtained from the model) versus the length of its projection footprint for a certain projection direction. Magnification can be accounted for by using the known imaging geometry. Other criteria include finding the direction with minimal overlap with other (possibly disturbing) structures, or at least by finding projection directions where overlap is within a given margin, where "overlap" is quantified as a suitable score such as ratios of area size, etc. In this manner, best alignment of anatomical features (such as valve cusps in cardiac imaging) can be achieved. In connection with the least overlap criterion, the earlier mentioned combo- or super-model m(OB) may be used with benefit as it not only, say, the guide wire that is represented in the super-model m(OB) but also at least a part of the surrounding anatomy of the patient, such as one or more branches of the vessel tree. Said differently and more generally, in the embodiment based on a super-model, a projection direction is sought out where self-overlaps are avoided or where the number of such overlaps is minimal or smaller than a pre-preprogrammed or user-adjustable maximum of admissible overlaps.

The optimal projection direction(s) can be found in a geometric search operation or purely geometrically. In a geometric search, a plurality of rays are cast through the object model at suitably defined angular increments (such as 1°-5° or others), to so produce a series of projection views, each encoding a projective footprint of the object. These projection footprints are then evaluated by computing the optimality scores and the projection direction that yields the best score or at least those whose score satisfied a given threshold is/are then forwarded to selector SX and are then processed as described to select the imaging pair(s) $IP_j$.

The optimal projection direction(s) may instead or in addition be computed by purely geometric computations, e.g., by finding a plane through a geometrical configuration of structures of interest in the model and to then establish the normal thereto. The geometrical structure is such that it admits definition of such as plane, such as three points or two non-parallel edge structures such as non-parallel branches of a vessel tree or respective tangents thereto. The curved or bent portion of the guide-wire tip likewise admits definition of such a "view plane" of interest. The normal vector of the plane is then the determined, optimal, projection direction. The direction of least overlap or of least foreshortening can be found in this manner. One, non-limiting, way to implement this is to set up an optimization function that represents the amount of foreshortening as a function of imaging coordinates and to then solve this function for optimal imaging coordinates using known optimization techniques. See for instance, section II, B in S J Chen et al in "3-D Reconstruction of Coronary Arterial Tree to Optimize Angiographic Visualization", IEEE TRANSACTIONS ON MEDICAL IMAGING, VOL. 19, NO. 4, APRIL 2000.

Rather than using each of these optimality criteria in the alternative, a combination of some or all of these criteria is also envisaged by setting up a combined score achieved in each of the applied criteria. The combined score may be formed as an average or weighted average of each of the separately achieved scores used for the different criteria.

The proposed control system SC enables optimized projection directions and therefore a better temporal sampling of the investigated object in these directions for interventions with fixed multi source-detector configurations. It may be applied for live-imaging of guide-wires, catheters or devices as well as bolus chasing in vascular trees. It can also be used for valve deployment in TAVI procedures which rely on an imaging with optimal projection direction.

The imaging control SC can be run wholly on a work station or other general purpose computing device having a processing unit PU, which may be associated with the imager IA for controlling its operation. As an alternative to this, implementation in a distributed computing architecture is also envisaged, where the system SC serves a plurality of imagers IA or where the tasks of at least one or all of the components are outsourced to other computing units in the network. At least one or all components of the system SC may be arranged in hardware such as in a suitably programmed FPGA (field-programmable-gate-array) or as a hardwired IC chip. For instance, the imaging control system SC may be integrated as a control module into the imaging apparatus IA.

Figure 3:
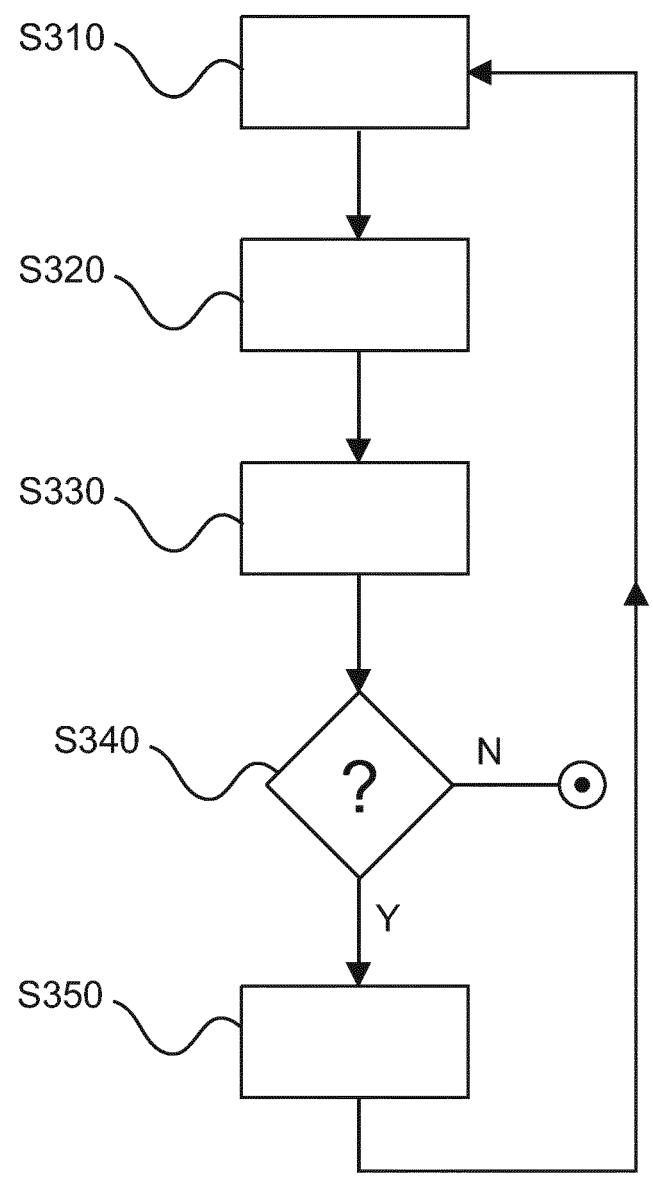
FIG. 3 shows a flow chart for a method of controlling operation of an X-ray imaging apparatus.

Reference is now made to the flow chart in FIG. 3 to explain a method of controlling the operation of a multi-focal-X-ray imaging apparatus. It should be noted that the following description of the method steps is not necessarily tied to the architecture as shown and explained in FIG. 1 and the following explanation may also be understood as a teaching in its own right.

At step S310 a projection direction is determined for an object to be imaged. This is based on a geometric structure of a model for the object. The object is preferably a 3D model and is prepared in a preparatory phase as suitable model such as a mesh model or centerline model, or otherwise. Preferably the model is de-formable to so model shape changes such as flexures, deformations of the object etc. The object may include medical tools such as a guide wire or others but the model may also be a super-model that includes the tool resident in the subject and parts/feature of the surrounding anatomy. The model is assumed registered in the examination space so the X-ray source or sources and the detector of the imager to be controlled are aligned in a common co-ordinate frame.

The determined projection direction is preferably an optimal one based on predefined optimality criteria. Criteria include minimal foreshortening, or minimal overlap of structures within the model, or others or a combination of these criteria. Optimal projection may be determined by a search operation in which a number of geometric rays are cast at angular increments through the 3D shape. The projection footprint in these projection views of the model or of sub-features therein is then evaluated against the criteria to determine the optimal projection direction(s). For example, a size (area, diameter, etc.) of the footprint in each projection is determined to find the projection direction where least foreshortening occurs.

In other embodiments, the criteria are evaluated purely geometrically. If the shape of the model or the geometrical configuration of features therein admits definition plane, the optimal direction may be defined as along a normal vector of this plane.

A combination (by forming averages etc.) of any of the above or other view quality criteria may be used in step S310 to determine one or more projection directions that best, or at least within a margin, satisfy the optimality condition/criterion or combination of conditions.

The output at the determining step S310 is not necessarily a single projection direction as a plurality of projection directions may satisfy the optimality criterion.

Based on the determined "ideal" projection direction, one or more imaging pairs of the multi-focal imager are then selected in step S320. In particular, an image pair is selected whose optical axis best corresponds to at least one of the determined projection direction(s). To "(best) correspond" means for present purposes to least deviate (in angular terms) from at least one of the projection directions or to at least fall within a defined angular margin of at least one of the determined projection directions.

In particular, a single one or a true sub-set of all available imaging pairs is selected to so define a single target pair or two or more target pairs. In particular, in one embodiment, a pair of imaging pairs is selected for the determined optimal projection directions as some multi-focal imagers use at each instant a pair of imaging pairs as illustrated above in the embodiment of FIG. 2.

At step S330 one or more images are then acquired only along the selected optical axis of the selected pair or pairs for the given imaging instant. This does not exclude however that other pairs are selected for follow-up images as will be explained now. In particular, Instead of updating the X-ray projections from all available source-detector pairs, only the selected imaging pairs are used. Consequently, a frame rate can be increased and the latency of the visualization will be reduced.

Indeed at step S340 it is determined whether a follow-up image is to be acquired. If no, then the method flow stops here.

If a follow-up image is to be acquired, flow control passes on to step S350 where the currently used model m(OB) is updated. This step is optional and may not always be acquired as the object may not have moved or changed its shape. Movement of the object can be established by optical flow analysis or segmentation or otherwise across the previously acquired images. The model can be updated by using automatic tip-tracking across the previously acquired images. The automatic tip-tracking can be used for instance when the object is a guide-wire. A model image is then acquired by tri-angulation as mentioned above and, based on this mode image, a new updated model having the new shape is obtained by using a suitable model generation technique (mesh model, line model, or otherwise).

There may also be an option to receive an adaptation request by the user through a suitable interface. In this manner the user can determine whether the model should be updated and can, for instance, define how the update is to occur. For instance, the user can prescribe a new shape, form or orientation, etc. of the current model.

Once a shape orientation or deformation of the model has been adapted or updated in step S350, flow control returns to step S310 where the previously described method is repeated based now on the new model to so produce a follow-up image acquired at a possibly newly selected imaging pair.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium (in particular, but not necessarily, a non-transitory medium), such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An imaging arrangement, comprising:
   a multi-focal spot X-ray imager of the non-rotational type, having a detector and an X-ray source defining a plurality of focal spots, the X-ray source being configured so that the focal spots define, with the detector, imaging pairs having different optical axes;
   a projection direction determiner configured to determine a projection direction for an object to be imaged based on a geometric structure of a model for the object; and
   a selector configured to select, from the plurality of imaging pairs, at least one target pair whose optical axis is within an angular margin $\Delta\alpha$ of the determined projection direction.

2. The imaging arrangement of claim 1, further comprising:
   an instruction module configured to instruct the imager to acquire an image of the object along the optical axis of the target pair.

3. The imaging arrangement of claim 1, further comprising:
   a model updater configured to update the model, the projection direction determiner then determining a new projection direction and/or the selector then selecting a new target pair.

4. The imaging arrangement of claim 1, wherein the determining of the projection direction by the projection direction determiner is based on any one or a combination of the following selection criteria:
   i) an amount of perspective foreshortening of the model or a part thereof in projection view,
   ii) an amount of perspective overlap of features of the model in projection view, or
   iii) a deviation from a normal vector of a plane defined by a geometric configuration of the model.

5. The imaging arrangement of claim 4, wherein a single target pair is selected whose optical axis deviates least from the determined projection direction.

6. The imaging arrangement of claim 5, wherein the imager includes at least one additional different X-ray source having different focal spot.

7. The imaging arrangement of claim 6, wherein the X-ray source has a spatially variable focal-spot.

8. The imaging arrangement of claim 1, wherein the detector and/or the X-ray source is/are fixedly mounted in a mounting structure.

9. The imaging arrangement of claim 8, wherein the imaging pairs are defined between the plurality of X-ray focal spots and associated sub regions of the detector.

10. A method of controlling operation of an X-ray imaging apparatus operable in a plurality of imaging pairs defined by a plurality of X-ray focal spots and a detector, the imaging pairs having different optical axes, the method comprising:

for an object to be imaged, determining a projection direction based on a geometric structure of a model for the object; and selecting, from the plurality of imaging pairs, a target pair whose optical axis is within an angular margin $\Delta\alpha$ of the determined projection direction.

11. The method of claim 10, further comprising:
acquiring an image of the object along the optical axis of the selected target pair.

12. The method of claim 11, wherein the image is acquired only along the optical axis of the target pair.

13. The method of claim 10, further comprising:
updating the model and determining a new projection direction and/or selecting a new target pair.

14. A non-transitory computer-readable medium having stored thereon a computer program having instructions, which, when being executed by a processing circuitry, causes the processing circuitry to:

for an object to be imaged, determine a projection direction based on a geometric structure of a model for the object; and select, from a plurality of imaging pairs, a target pair whose optical axis is within an angular margin $\Delta\alpha$ of the determined projection direction, wherein the plurality of imaging pairs are defined by a plurality of X-ray focal spots and a detector, the imaging pairs having different optical axes.

15. The non-transitory computer-readable medium of claim 14, wherein the instructions, which, when being executed by the processing circuitry, cause the processing circuitry to acquire an image of the object along the optical axis of the selected target pair.

16. The non-transitory computer-readable medium of claim 15, wherein the image is acquired only along the optical axis of the target pair.

17. The non-transitory computer-readable medium of claim 14, wherein the instructions, when executed by the processing circuitry, cause the processing circuitry to update the model and determine a new projection direction or select a new target pair.

* * * * *